United States Patent
Denis et al.

[11] Patent Number: 5,883,289
[45] Date of Patent: *Mar. 16, 1999

[54] PREPARATION OF CARBOXYLIC ACIDS OR RELATED ESTERS BY CARBONYLATION IN THE PRESENCE OF IRIDIUM

[75] Inventors: Philippe Denis, Decines; Dominique Nobel, Salindres; Robert Perron, Charly; Joël Andre Schwartz, Caluire, all of France

[73] Assignee: Acetex Chimie, Paris, France

[*] Notice: This patent issued on a continued prosecution application filed under 37 CFR 1.53(d), and is subject to the twenty year patent term provisions of 35 U.S.C. 154(a)(2).

[21] Appl. No.: 809,706
[22] PCT Filed: Oct. 4, 1995
[86] PCT No.: PCT/FR95/01283
   § 371 Date: May 14, 1997
   § 102(e) Date: May 14, 1997
[87] PCT Pub. No.: WO96/11179
   PCT Pub. Date: Apr. 18, 1996

[30] Foreign Application Priority Data

Oct. 5, 1994 [FR] France .................................. 94 12044

[51] Int. Cl.$^6$ ............................ C07C 67/36; C07C 51/12
[52] U.S. Cl. ........................ 560/232; 562/517; 562/519; 562/520
[58] Field of Search ............................. 560/232; 562/517, 562/519, 520

[56] References Cited

U.S. PATENT DOCUMENTS

| | | | |
|---|---|---|---|
| 4,482,497 | 11/1984 | Rizkalla | 260/413 |
| 4,681,707 | 7/1987 | Alper et al. | 260/410.9 R |
| 5,144,068 | 9/1992 | Smith et al. | 562/519 |
| 5,420,345 | 5/1995 | Smith | 562/519 |

FOREIGN PATENT DOCUMENTS 0 616 997  9/1994  France .

*Primary Examiner*—Gary Giest
*Assistant Examiner*—Rosalynd Keys
*Attorney, Agent, or Firm*—Dennison, Meserole, Pollack & Scheiner

[57] ABSTRACT

A method for preparing carboxylic acids including (n+1) carbon atoms, or the related esters, by liquid phase carbonylation of an alcohol including (n) carbon atoms, in the presence of a uniform catalytic system based on at least one iridium compound and at least one halogenated promoter. In particular, the method is characterised in that the content of ester related to said carboxylic acid and alcohol is kept between 15 and 35% in the medium during the reaction, while the halogenated promoter content is kept between 10 and 20%, and the partial carbon monoxide pressure is 40–200 bar. Said method enables both the rate of carbonylation and the acetic acid selectivity to be increased.

13 Claims, No Drawings

PREPARATION OF CARBOXYLIC ACIDS OR RELATED ESTERS BY CARBONYLATION IN THE PRESENCE OF IRIDIUM

BACKGROUND OF THE INVENTION

The present invention relates to a method for preparing carboxylic acids having (n+1) carbon atoms, or the related esters, by liquid phase carbonylation of an alcohol having (n) carbon atoms, in the presence of a homogeneous catalyst including iridium.

More particularly, the method according to the invention enables obtaining a high productivity of carboxylic acid formed with an improved selectivity in this product.

During carboxylic acid preparation by reaction of carbon monoxide with at least one alcohol, two catalytic cycles are used, the first is constituted by the carbonylation reaction as such, and the second by a secondary reaction, commonly called water gas reaction. During this reaction, gaseous by-products are formed such as notably carbon dioxide.

Thus, the object to be achieved is obviously to favour the first reaction over the second.

The carbonylation of an alcohol, or any other carbonylatable compound, in the presence of an iridium-based catalytic system giving the corresponding carboxylic acid or ester is known to the person skilled in the art. However, such methods are not very efficient since the rates of carbonylation that are reported are in the order of 2 to 4 mol/hour.liter of acid formed.

In the French patent application No. 93 03734, a method of carbonylating methanol is described which uses a catalytic system which comprises iridium. This method is characterised by the maintenance of a specific composition of the reaction mixture. In the case of obtaining acetic acid from methanol, the composition comprises up to 10% water, alcohol and methyl iodide; up to 40% methyl acetate; the rest being constituted by acetic acid which is used as reaction solvent. The tests described have been carried out with relatively low partial carbon monoxide pressures, in the order of 10 to 20 bar. The performances of this method are appreciably improved over those of prior methods, and the technical interest of the latter is not questioned. However, the selectivity in by-products such as carbon dioxide remains high, since it ranges between 1 and 2%.

Furthermore, a carbonylation method is described in the French patent application No. 94 05896 which uses a catalytic system comprising iridium and iodides which are soluble in the reaction medium under the reaction conditions, and which are notably selected from alkali metal iodides. The performances, in terms of rate of carbonylation are there further improved over the prior methods, but the problem of the selectivity in carbon dioxide always exists. In fact, the selectivities in this by-product range between 1 and 3%.

Such values are not negligible in this sense that they correspond to relatively significant losses of carbon monoxide; losses which are felt in two ways. First of all, and obviously, the carbon monoxide employed is consumed for something other than the formation of the acid or the ester. Further, an additional loss is noted in carbon monoxide, due to the necessity of increasing the number of purges and consequently increasing the losses in carbon monoxide brought about during the evacuation of the gases. In fact, the appearance of gaseous by-products contributes to the lowering of the partial carbon monoxide pressure in the gaseous blanket of the reactor, resulting in the necessity of increasing the number of purges in order to maintain said partial pressure constant.

SUMMARY OF THE INVENTION

Therefore, an object of the present application is to alleviate this type of disadvantage, at least in keeping, even improving the rate of carbonylation of the reaction.

It has been found in a totally surprising way that such objects could be attained by carrying out the carbonylation reaction in the presence of a high content of ester and methyl iodide, in combination with a significant partial carbon monoxide pressure.

Thus, the method according to the invention consists in reacting carbon monoxide with at least one alcohol, in the liquid phase and in the presence of a catalytic system based on at least one iridium compound and at least one halogenated promoter; a method in which, during the reaction, the ester corresponding to the aforementioned acid and alcohol is kept in the reaction medium at a content between 15 and 35%, the halogenated promoter at a content between 10% and 20%, and a partial carbon monoxide pressure is between 40 and 200 bar.

Other goals and advantages of the present invention will however appear more clearly upon reading the description which will follow.

In the following, and unless otherwise indicated, the percentages indicated are expressed by weight compared to the total weight of the reaction mixture.

DETAILED DESCRIPTION OF THE INVENTION

Such as has been said previously, the carbonylation reaction of the invention is carried out in the presence of a catalytic system based on at least one iridium compound and at least one halogenated promoter.

The reaction being carried out in the liquid phase, the catalytic system is in the form of compounds which are soluble in the reaction mixture.

All the iridium compounds may be used which are soluble or capable of being dissolved in the reaction medium under the operating conditions of the invention. As an example and without the intention of limiting, metallic iridium, simple salts, oxides or even co-ordination complexes of this metal can be convenient for implementing the invention. For more details, the U.S. Pat. No. 3,772,380 may be referred to in which a list indicative of such compounds is given.

More particularly, simple salts of iridium are used, such as iridium halides, the halogen being selected from chlorine, bromine or preferably iodine.

The iridium oxides, as for the soluble iridium co-ordination complexes, are convenient for implementing the invention. In this latter category, the most commonly used compounds are those which have ligands selected from carbon monoxide or a carbon monoxide/halogen combination, the halogen being selected from chlorine, bromine or more particularly iodine. It is not however excluded to use soluble iridium complexes whose ligands are selected from organophosphorus or organonitrogen compounds for example.

These catalysts may be obtained by any method known to the person skilled in the art.

However, according to a particularly advantageous method, a catalytic solution may be prepared from a carbonyl complex of iridium, such as $Ir_4CO_{12}$, by placing said compound in contact with hydroiodic acid and/or a precursor of such an acid, in the presence of a solvent.

Iodine, $C_1$–$C_{10}$ alkyl iodides, $C_1$–$C_{10}$ alkoyl iodides, or even alkali metal iodides may be mentioned as examples of a precursor which is capable of releasing hydroiodic acid.

As for the solvents, all the compounds may be used insofar as they solubilize hydroiodic acid or its precursor and the iridium-based compound obtained. More particularly, solvents selected from carboxylic acids or the corresponding esters are used which are obtained by the method according to the invention, water can be used; these compounds being used alone or in a mixture.

The placing in contact takes place under a total pressure of between 1 and 10 bar, at a temperature at the most equal to the boiling point of the above-mentioned solvent, under the conditions of the placing in conditions of the placing in contact.

The operation may be carried out under air, under an inert gas or even under carbon monoxide.

Another example of an advantageous method for preparing a catalytic solution which is convenient for the implementation of the invention consists in placing one or more hydrated or non-hydrated iridium oxides in contact with hydroiodic acid or a compound capable of releasing hydroiodic acid, in the liquid phase. The hydroiodic acid may be employed as a gas, a solution, and more particularly an aqueous solution. It may even be used in the form of a precursor, such as those mentioned in the preceding variant.

More particularly, the amount of hydroiodic acid used is such that the ratio of the number of moles of hydroiodic acid to the number of moles of iridium is between 1 and 100.

This variant of preparation of a catalytic solution may be used under air, under an inert gas, under carbon monoxide, these gases being alone or in combination.

The total iridium concentration in the mixture used in the method according to the invention is between 0.1 and 100 mmol/l.

According to a particular embodiment, the iridium concentration is from 0.5 to 40 mmol/l and preferably between 1 and 25 mmol/l.

The second constituent of the catalytic system is a halogenated promoter. This may be in the form of a halogen alone or in combination with other elements, such as for example hydrogen, a $C_1$–$C_{10}$ alkyl radical, a $C_1$–$C_{10}$ acyl radical, or a $C_6$–$C_{10}$ aryl radical.

The halogen is generally selected from chlorine, bromine or iodine, the latter being preferred.

According to a particular embodiment of the invention, the halogenated promoter used comprises, besides the halogen, hydrogen or a $C_1$–$C_{10}$ alkyl radical. More particularly, the promoter used in the invention comprises the halogen and a $C_1$–$C_{10}$ alkyl radical.

Preferably, the reaction according to the invention is carried out in the presence of a halogenated promoter whose radical corresponds to that of the alcohol used as reagent.

The halogenated promoter content in the medium is between 10 and 20%.

According to a particular embodiment, the halogenated promoter content varies between 10 (excluded) and 20%.

A variant of the invention consists in keeping the halogenated promoter content in the reaction medium between 10 (excluded) and 15%.

The method according to the invention is furthermore carried out in the presence of carbon monoxide. This may be used pure or diluted in gases such as hydrogen, methane, carbon dioxide, or any other type of gas such as for example nitrogen.

According to a particular embodiment of the invention, carbon monoxide having a purity of at least 99% is used.

The method according to the invention is carried out in keeping a partial carbon monoxide pressure between 40 and 200 bar during the reaction.

According to a first variant, the partial pressure is between 40 and 70 bar. More particularly, the partial carbon monoxide pressure is between 50 and 70 bar.

According to a second variant, the partial carbon monoxide pressure is between 70 bar (excluded) and 200 bars. Without being limited to such an alternative, the use of such partial pressures makes it possible to carry out the reaction at lower temperatures than those in methods carried out at lower pressures. This represents notably an advantage as far as the corrosivity of the reaction medium is concerned.

The method according to the invention is carried out in the presence of esters which correspond to the reaction of the alcohol used in the reaction with the carboxylic acid present in the reaction medium.

According to a characteristic of the method of the invention, the ester content in said medium is between 15 and 35%.

A particular embodiment consists in carrying the reaction out in keeping an amount of ester between 15 and 25%.

According to a particular embodiment, the ester content is between 18 and 23%. It is to be noted that this variant is particularly convenient when the carbonylation reaction is carried out under low partial carbon monoxide pressures, i.e. between 40 and 70 bar.

The carbonylation reaction according to the invention is further carried out in the presence of water. The water content in the medium is between 0 (excluded) and 15%.

More particularly, the water content in the medium is between 0 (excluded) and 10%.

Such as has been indicated before, at least one alcohol having one carbon atom less than the carboxylic acid produced, or the corresponding ester is used as reagent.

Amongst the reagents which are convenient for carrying out the reaction, saturated alcohols having one to six carbon atoms may be cited. These alcohols may be mono- or di-hydroxylated. As an example of such compounds, methanol, ethanol, propanol, butanol and 1,4-butanediol may notably be cited.

According to a preferred embodiment, the alcohols used are selected from monohydroxylated compounds.

It is important to note that the alcohol used as reagent may be present in the reaction medium as such or in a masked form. In fact, said alcohol may be found equally in the form of a halogenated derivative and/or an ether and/or an ester.

The reagent content in the reaction medium can thus be between large limits, this being due to the various species under which the reagent may be.

Consequently, the content of alcohol, as such, in the reaction medium may be between 0 and 10%. Preferably, the medium has an alcohol content of between 0.1 and 5%.

According to a first embodiment of the invention, the reaction is carried out in the presence of ionic compounds which are soluble in the reaction medium and of which one of the ions is iodine (from now on these compounds shall be referred to as iodides). The iodides may be introduced as such into the reaction medium but also may be introduced in the form of compounds which are capable of forming soluble iodides.

Thus, the iodides introduced as such into said mixture are selected from inorganic or organic iodides.

As inorganic iodides, the alkaline-earth or alkali metal iodides may be cited, the latter being preferred. For example, potassium iodide, lithium iodide, sodium iodide are convenient for the implementation of the invention.

As organic iodides, the organic compounds having at least one organophosphorus and/or at least one organonitrogen group may be cited which reacts with iodine-based compounds giving ionic species which contain this halogen. As an example, triphenylphosphonium iodide and N-methyltriethylammonium iodide may be mentioned.

Amongst the compounds which are capable of forming iodides which are soluble in the reaction medium, the alkali metal or alkaline-earth metal carboxylates are notably convenient, such as especially lithium acetate.

More particularly, the reaction is carried out in the presence of an amount of iodides which depends upon the amount of iridium present in the medium. Thus, this amount of iodides introduced is such that the iodine (originating from the iodides)/iridium atomic ratio (expressed in mole/mole), is kept at a value at the most equal to 10.

Preferably, the atomic ratio is at the most equal to 3.

According to a second implementation of the invention, the method is carried out in the absence of soluble iodides such as defined above.

Finally, the method according to the invention is carried out in a solvent which, preferably, corresponds to the carboxylic acid formed by the reaction.

Such as has been indicated before, the present invention consists in keeping the halogenated promoter, the above-mentioned ester, a partial carbon monoxide pressure, optionally the iodides, water and the carboxylic acid, in the reaction mixture in proportions which have just been clarified.

Consequently, the present invention is more particularly intended to be used continuously and the stable functioning conditions of the method correspond to the composition and the proportions indicated.

During the starting up of the reaction, the various components are introduced in an appropriate reactor equipped with a means of stirring which is sufficient for ensuring the gas-liquid transfer. It is to be noted that if the reactor preferably comprises a means of mechanical stirring, operating without such means is not excluded; the homogenization of the mixture can be carried out by the introduction of the carbon monoxide into the reactor.

The components of the reaction medium are introduced without preferential order, and are introduced as they are and/or as one or more precursors.

A first variant of the invention consists in introducing the halogenated precursor described above, as it is, into the reaction mixture.

A second variant of implementation consists in introducing said promoter in the form of at least one precursor.

In this particular case, this precursor is generally in the form of a compound which is capable of releasing the radical of the above-mentioned halogenated promoter into the reaction medium by reaction of said precursor with a halogen, the corresponding hydroacid, or an iodide, present in the medium or even introduced to this end.

As a non-limiting example of suitable precursors, compounds selected from alcohols of formula (1) ROH; ethers of formula (2) ROR' or even esters of formulae (3) R'COOR, used alone or in a mixture, may be cited. In these formulae, R and R' radicals, identical or different, each represent a $C_1$–$C_{10}$ alkyl radical, a $C_1$–$C_{10}$ acyl radical, a $C_6$–$C_{10}$ aryl radical; with the R radical corresponding to the radical of the halogenated promoter.

Thus, methanol, ethanol, propanol, butanol, dimethyl ether, diethyl ether, ethylene oxide, methyl acetate, are especially suitable precursors of the halogenated promoter.

The carbonylation is usually carried out at a temperature between 150° and 250° C. According to a variant, the reaction temperature is between 150° and 210° C.

The total pressure in the reactor is between 50 and 250 bar.

It is to be noted that the method according to the invention may be conveniently used in installations which make use of conventional methods.

These methods are thus usually constituted of three zones. The first corresponds to the reaction zone which comprises a reactor under pressure. The second is that of separation of the acid formed, or of the corresponding ester, by partial vaporisation of the reaction mixture. The vaporised part is then sent into the third zone, which is that of purification of the carboxylic acid or the corresponding ester. The part of the mixture which has remained in the liquid form in the partial vaporisation zone, which comprises notably the catalyst, is recycled to the reactor.

According to a particular embodiment of the method according to the invention, the reaction mixture is regularly purged of the corrosive metals that it contains, of which are notably iron, molybdenum, chromium, and nickel. This operation is carried out according to any means which is known to the person skilled in the art, such as for example the treatment of the reaction mixture by an ion exchange resin or even by precipitation of the catalyst and separation of the latter, corrosive metals, by filtration.

The method according to the invention is convenient for the manufacture of any type of carboxylic acid which has a minimum of two carbon atoms, or of the corresponding ester. Thus, this may be used for preparing propionic acid from ethanol, succinic acid from ethylene oxide, adipic acid from 1,4-batanediol, or the esters corresponding to these acids.

However, this method is most particularly convenient for obtaining acetic acid and/or methyl acetate from methanol.

According to a preferred embodiment of the invention, the method is carried out with methyl iodide, methyl acetate, optionally above-mentioned iodides, water and acetic acid as solvent, besides methanol and carbon monoxide.

Examples of the invention, which are concrete and not limiting, are now going to be given.

EXAMPLES

The following tests were carried out continuously in a 300 cm$^3$ autoclave equipped with a means of mechanical stirring and a means of introducing the reagents.

The catalytic solution was obtained in the following way:
  10 g of $Ir_4(CO)_{12}$, 50 g of hydroiodic acid in a 57% solution in water, and 290 g of acetic acid are introduced into a glass flask.

The mixture is then heated under reflux with stirring and under air for 4 hours.

The introductions of methanol, methyl iodide and water are regulated in such a way that the content of the various components, as well as the partial carbon monoxide pressure and the total pressure are maintained as indicated in the following Table.

It is to be noted that the water content remains between 6 and 8% and that the methanol content is between 0.1 and 2%. Furthermore, the rest making up 100% is constituted of acetic acid which is employed as a solvent of the reaction.

The staying time in the reactor is about 10 minutes.

The temperature is kept at 190° C.

Upon leaving the autoclave, the reaction mixture is degassed and cooled.

The mixture and the gases are analysed by gas phase chromatography.

| TEST | $CH_3CO_2CH_3$ (% weight) | $CH_3I$ (% weight) | $P_{CO}/P_{tot}$ (bars) | Ir (ppm) | $V_{carb}$ (mol/h.l) | Selectivity $CO_2$ (%) |
|---|---|---|---|---|---|---|
| A comparative | 10 | 4 | 18/30 | 680 | 6.2 | 2.2 |
| B comparative | 11 | 11 | 40/52 | 800 | 8.4 | 1.4 |
| C comparative | 18 | 3.6 | 18/30 | 640 | 8.6 | 1.4 |
| D | 23 | 11 | 40/52 | 700 | 16 | 0.6 |

$V_{carb}$ represents the rate of carbonylation. It is obtained by measuring the flow of CO consumption in further taking into account the amount of this gas used up in the formation of $CO_2$.

The rate of $CO_2$ formation is checked by measuring the flow of formation of the $CO_2$. This value enables calculating the selectivity in $CO_2$ which corresponds to the ratio of the speed of formation of the $CO_2$ and the rate of carbonylation.

This Table indicates that improved performances are not obtained in terms of rate of carbonylation and selectivity when one or more of the reaction parameters is found outside the characteristics of the invention.

What is claimed is:

1. Method for preparing a carboxylic acid having (n+1) carbon atoms, or a corresponding ester, by liquid phase carbonylation of an alcohol having (n) carbon atoms, comprising reacting carbon monoxide with said at least one alcohol having (n) carbon atoms, in a liquid phase reaction medium and in the presence of a catalytic system based on at least one iridium compound and at least one halogenated promoter, further comprising maintaining in said reaction medium during said reacting an ester corresponding to said carboxylic acid and alcohol at a content between 15 and 35% by weight, the halogenated promoter at a content of between 10 and 20% by weight, and carbon monoxide at a partial pressure between 40 and 200 bar, to thereby increase carbonylation rate and improve selectivity.

2. Method according to claim 1, wherein the partial carbon monoxide pressure is maintained between 40 and 70 bar.

3. Method according to claim 1, wherein the partial carbon monoxide pressure is maintained between 70 bar (excluded) and 200 bar.

4. Method according to claim 1, wherein the halogenated promoter content is greater than 10% by weight and no more than 20% by weight.

5. Method according to claim 1, wherein the ester content is maintained between 15 and 25% by weight.

6. Method according to claim 1, wherein the ester content is maintained between 18 and 23% by weight.

7. Method according to claim 1, wherein water is present in the reaction medium at a content of no more than 15% by weight.

8. Method according to claim 1, wherein the reacting is carried out in the presence of at least one ionic compound which is soluble in the reaction mixture and of which includes an iodine ion.

9. Method according to claim 8, wherein the iodine is maintained such that iodine and iridium are present in an iodine/iridium atomic ratio at most equal to 10.

10. Method according to claim 1, wherein the carboxylic acid is acetic acid prepared by reaction of methanol with carbon monoxide in the presence of methyl iodide, methyl acetate, optionally at least one soluble ionic compound, water and acetic acid as a reaction solvent.

11. Method according to claim 2, wherein the partial carbon monoxide pressure is between 50 and 70 bar.

12. Method according to claim 4, wherein the halogenated promoter is maintained at a content of no more than 15% by weight.

13. Method according to claim 7, wherein the water content is no more than 10% by weight.

* * * * *